United States Patent
White et al.

(10) Patent No.: US 12,419,753 B2
(45) Date of Patent: Sep. 23, 2025

(54) ORTHOPAEDIC SYSTEM WITH MEDIAL PIVOTING FEMORAL COMPONENT AND INSERT

(71) Applicant: DEPUY IRELAND UNLIMITED COMPANY, Ringaskiddy (IE)

(72) Inventors: Stephen E. White, Fort Wayne, IN (US); William J. Maloney, Palo Alto, CA (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 1004 days.

(21) Appl. No.: 17/438,213

(22) PCT Filed: Mar. 11, 2020

(86) PCT No.: PCT/US2020/022119
§ 371 (c)(1),
(2) Date: Sep. 10, 2021

(87) PCT Pub. No.: WO2020/185908
PCT Pub. Date: Sep. 17, 2020

(65) Prior Publication Data
US 2022/0175541 A1 Jun. 9, 2022

Related U.S. Application Data

(60) Provisional application No. 62/817,173, filed on Mar. 12, 2019.

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2002/30326* (2013.01); *A61F 2002/30327* (2013.01); *A61F 2002/3863* (2013.01)

(58) Field of Classification Search
CPC .................. A61F 2/3859; A61F 2/389; A61F 2002/30326; A61F 2002/30327; A61F 2002/3863
See application file for complete search history.

(56) References Cited

U.S. PATENT DOCUMENTS 3,748,662 A 7/1973 Helfet
4,216,549 A 8/1980 Hillberry et al.
(Continued)

FOREIGN PATENT DOCUMENTS

CN 102596107 A 7/2012
CN 103118635 A 5/2013
(Continued)

OTHER PUBLICATIONS

Notice of Reasons for Refusal, JP Application No. 2021-554721, Nov. 30, 2023 (6 pages).
(Continued)

*Primary Examiner* — Bruce E Snow
(74) *Attorney, Agent, or Firm* — Barnes & Thornburg LLP (57) ABSTRACT

An orthopaedic system includes a tibial insert and a femoral component configured to articulate on the tibial insert. The tibial insert includes an articular surface, and the femoral component includes a femoral articular surface having decreasing radii of curvature posteriorly. The articular surface of the tibial insert includes an increased anterior lip to improve stability of the femoral component.

14 Claims, 5 Drawing Sheets

(56) References Cited

U.S. PATENT DOCUMENTS

| | | | |
|---|---|---|---|
| 4,944,757 A | 7/1990 | Martinez et al. |
| 5,219,362 A | 6/1993 | Tuke et al. |
| 5,271,737 A | 12/1993 | Baldwin et al. |
| 5,344,460 A | 9/1994 | Turanyi et al. |
| 5,356,414 A | 10/1994 | Cohen et al. |
| 5,370,701 A | 12/1994 | Finn |
| 5,405,349 A | 4/1995 | Burkinshaw et al. |
| 5,486,178 A | 1/1996 | Hodge |
| 5,658,341 A | 8/1997 | Delfosse |
| 5,662,656 A | 9/1997 | White |
| 5,667,512 A | 9/1997 | Johnson |
| 5,682,886 A | 11/1997 | Delp et al. |
| 5,709,689 A | 1/1998 | Ferrante et al. |
| 5,735,856 A | 4/1998 | Mccue et al. |
| 5,769,854 A | 6/1998 | Bastian et al. |
| 5,782,925 A | 7/1998 | Collazo et al. |
| 5,810,829 A | 9/1998 | Elliott et al. |
| 5,871,018 A | 2/1999 | Delp et al. |
| 5,964,808 A | 10/1999 | Blaha et al. |
| 5,976,147 A | 11/1999 | Lasalle et al. |
| 6,013,103 A | 1/2000 | Kaufman et al. |
| 6,033,410 A | 3/2000 | Mclean et al. |
| 6,258,095 B1 | 7/2001 | Lombardo et al. |
| 6,506,215 B1 | 1/2003 | Letot et al. |
| 6,986,791 B1 | 1/2006 | Metzger |
| 7,081,137 B1 | 7/2006 | Servidio |
| 7,115,133 B2 | 10/2006 | Plumet et al. |
| 7,261,740 B2 | 8/2007 | Tuttle et al. |
| 7,625,407 B2 | 12/2009 | Akizuki et al. |
| 7,674,268 B2 | 3/2010 | Cuckler et al. |
| 7,695,519 B2 | 4/2010 | Collazo |
| 7,731,755 B2 | 6/2010 | Wyss et al. |
| 7,740,662 B2 | 6/2010 | Barnett et al. |
| 8,187,335 B2 | 5/2012 | Wyss et al. |
| 8,192,498 B2 | 6/2012 | Wagner et al. |
| 8,211,181 B2 | 7/2012 | Walker |
| 8,236,061 B2 | 8/2012 | Heldreth et al. |
| 8,292,964 B2 | 10/2012 | Walker |
| 8,328,873 B2 | 12/2012 | Metzger et al. |
| 8,382,846 B2 | 2/2013 | Samuelson et al. |
| 8,480,752 B2 | 7/2013 | Dun |
| 8,480,762 B2 | 7/2013 | Yoshimitsu |
| 8,586,486 B2 | 11/2013 | Chen et al. |
| 8,617,250 B2 | 12/2013 | Metzger |
| 8,628,579 B2 | 1/2014 | Ries et al. |
| 8,771,280 B2 | 7/2014 | Bailey et al. |
| 8,784,496 B2 | 7/2014 | Wagner et al. |
| 8,795,380 B2 | 8/2014 | Heldreth et al. |
| 8,808,388 B2 | 8/2014 | Mckinnon et al. |
| 8,828,086 B2 | 9/2014 | Williams et al. |
| 8,834,575 B2 | 9/2014 | Wyss et al. |
| 8,915,965 B2 | 12/2014 | Komistek |
| 9,050,107 B2 | 6/2015 | Sordelet et al. |
| 9,101,393 B2 | 8/2015 | Jordan et al. |
| 9,101,394 B2 | 8/2015 | Arata et al. |
| 9,168,145 B2 | 10/2015 | Wyss et al. |
| 9,216,088 B2 | 12/2015 | Wasielewski |
| 9,220,600 B2 | 12/2015 | Mihalko et al. |
| 9,220,601 B2 | 12/2015 | Williams et al. |
| 9,282,981 B2 | 3/2016 | Chaney et al. |
| 9,283,082 B2 | 3/2016 | Sanford et al. |
| 9,295,557 B2 | 3/2016 | Wentorf et al. |
| 9,299,138 B2 | 3/2016 | Zellner et al. |
| 9,320,616 B2 | 4/2016 | Samuelson et al. |
| 9,320,624 B2 | 4/2016 | Shin |
| 9,326,864 B2 | 5/2016 | Wyss et al. |
| 9,402,726 B2 | 8/2016 | Linderman et al. |
| 9,452,053 B2 | 9/2016 | Wagner et al. |
| 9,539,099 B2 | 1/2017 | Heldreth et al. |
| 9,603,711 B2 | 3/2017 | Bojarski et al. |
| 9,668,870 B2 | 6/2017 | Wasielewski |
| 9,707,088 B2 | 7/2017 | Samuelson et al. |
| 9,730,745 B2 | 8/2017 | Biedermann et al. |
| 9,788,954 B2 | 10/2017 | Parisi et al. |
| 9,820,821 B2 | 11/2017 | Aram et al. |
| 9,861,446 B2 | 1/2018 | Lang |
| 9,861,490 B2 | 1/2018 | Wentorf et al. |
| 9,931,216 B2 | 4/2018 | Williams et al. |
| 9,937,049 B2 | 4/2018 | Wyss et al. |
| 9,962,264 B2 | 5/2018 | Komistek |
| 10,080,663 B2 | 9/2018 | Wasielewski |
| 10,159,530 B2 | 12/2018 | Lang |
| 10,179,051 B2 | 1/2019 | Heldreth et al. |
| 10,179,052 B2 | 1/2019 | Clary et al. |
| 10,195,056 B2 | 2/2019 | Wogoman et al. |
| 10,201,429 B2 | 2/2019 | Enomoto et al. |
| 10,265,180 B2 | 4/2019 | Wyss et al. |
| 10,278,827 B2 | 5/2019 | Drury et al. |
| 10,478,307 B2 | 11/2019 | Wasielewski et al. |
| 10,543,098 B2 | 1/2020 | Williams et al. |
| 10,729,551 B2 | 8/2020 | Heldreth et al. |
| 10,849,760 B2 | 12/2020 | Wyss et al. |
| 11,141,291 B2 | 10/2021 | Wogoman et al. |
| 11,160,659 B2 | 11/2021 | Drury et al. |
| 11,229,485 B2 | 1/2022 | Otto et al. |
| 11,324,598 B2 | 5/2022 | Dai et al. |
| 11,337,823 B2 | 5/2022 | Williams et al. |
| 11,364,081 B2 | 6/2022 | Dees, Jr. |
| 11,369,478 B2 | 6/2022 | Wyss et al. |
| 11,612,488 B2 | 3/2023 | Wogoman et al. |
| 11,865,011 B2 | 1/2024 | Heldreth |
| 2002/0161448 A1 | 10/2002 | Hayes, Jr. et al. |
| 2003/0009228 A1 | 1/2003 | Figueroa et al. |
| 2003/0055509 A1 | 3/2003 | Mccue et al. |
| 2005/0075638 A1 | 4/2005 | Collazo |
| 2005/0096747 A1 | 5/2005 | Tuttle et al. |
| 2005/0107886 A1 | 5/2005 | Crabtree et al. |
| 2005/0278035 A1 | 12/2005 | Wyss et al. |
| 2007/0185581 A1 | 8/2007 | Akizuki et al. |
| 2008/0161918 A1 | 7/2008 | Fankhauser et al. |
| 2008/0262812 A1 | 10/2008 | Arata et al. |
| 2008/0269596 A1 | 10/2008 | Revie et al. |
| 2009/0088860 A1 | 4/2009 | Romeis et al. |
| 2009/0125114 A1 | 5/2009 | May et al. |
| 2009/0204221 A1 | 8/2009 | Walker |
| 2009/0306786 A1 | 12/2009 | Samuelson |
| 2010/0010635 A1 | 1/2010 | Straszheim-Morley et al. |
| 2010/0036499 A1 | 2/2010 | Pinskerova |
| 2010/0161067 A1 | 6/2010 | Saleh et al. |
| 2010/0168753 A1 | 7/2010 | Edwards et al. |
| 2010/0286788 A1 | 11/2010 | Komistek |
| 2010/0305711 A1 | 12/2010 | Mckinnon et al. |
| 2011/0153026 A1 | 6/2011 | Heggendorn et al. |
| 2012/0035737 A1 | 2/2012 | Sanford et al. |
| 2012/0197409 A1 | 8/2012 | Mckinnon et al. |
| 2012/0265496 A1 | 10/2012 | Mahfouz |
| 2012/0310246 A1 | 12/2012 | Belcher et al. |
| 2012/0310362 A1 | 12/2012 | Li et al. |
| 2013/0006373 A1* | 1/2013 | Wyss ............... A61F 2/3886 623/20.27 |
| 2013/0006376 A1 | 1/2013 | Gorab et al. |
| 2013/0006378 A1 | 1/2013 | Wogoman |
| 2013/0197653 A1 | 8/2013 | Hawkins et al. |
| 2013/0197654 A1 | 8/2013 | Samuelson et al. |
| 2013/0325021 A1 | 12/2013 | Sordelet et al. |
| 2014/0039635 A1 | 2/2014 | Bartels et al. |
| 2014/0052268 A1 | 2/2014 | Sanford et al. |
| 2014/0081412 A1 | 3/2014 | Metzger |
| 2014/0148811 A1 | 5/2014 | Reeve et al. |
| 2014/0277534 A1 | 9/2014 | Wasielewski |
| 2014/0277537 A1 | 9/2014 | Todd et al. |
| 2014/0330388 A1 | 11/2014 | Mizuguchi et al. |
| 2015/0032215 A1 | 1/2015 | Slamin et al. |
| 2015/0088264 A1 | 3/2015 | Li et al. |
| 2015/0190235 A1 | 7/2015 | McMinn |
| 2016/0030184 A1 | 2/2016 | Whiteside |
| 2016/0262771 A1 | 9/2016 | Edwards |
| 2016/0317312 A1 | 11/2016 | Bojarski et al. |
| 2017/0020674 A1 | 1/2017 | Walker |
| 2017/0079801 A1 | 3/2017 | Drury et al. |
| 2017/0128219 A1 | 5/2017 | Metzger et al. |
| 2017/0189191 A1 | 7/2017 | Heldreth et al. |
| 2017/0189195 A1 | 7/2017 | Blaha |
| 2017/0266013 A1 | 9/2017 | Enomoto et al. |

(56) References Cited

U.S. PATENT DOCUMENTS

| | | |
|---|---|---|
| 2017/0340389 A1 | 11/2017 | Otto et al. |
| 2019/0209331 A1 | 7/2019 | Varadarajan et al. |
| 2019/0209333 A1 | 7/2019 | Drury et al. |
| 2019/0240032 A1 | 8/2019 | Wasielewski et al. |
| 2020/0069432 A1 | 3/2020 | Mcminn |
| 2020/0085583 A1 | 3/2020 | Hodge |
| 2020/0100902 A1 | 4/2020 | Wasielewski et al. |
| 2020/0214843 A1 | 7/2020 | Radermacher et al. |
| 2020/0246149 A1 | 8/2020 | Matyas et al. |
| 2020/0268520 A1 | 8/2020 | Pak et al. |
| 2022/0079678 A1 | 3/2022 | Duxbury et al. |

FOREIGN PATENT DOCUMENTS

| | | |
|---|---|---|
| CN | 103327937 A | 9/2013 |
| CN | 108135701 A | 6/2018 |
| EP | 1604623 A1 | 12/2005 |
| EP | 2572677 A1 | 3/2013 |
| EP | 3854353 A1 | 7/2021 |
| JP | 2006015133 A | 1/2006 |
| JP | 2010012253 A | 1/2010 |
| JP | 2010012255 A | 1/2010 |
| JP | 2012513254 A | 6/2012 |
| JP | 2014510562 A | 5/2014 |
| JP | 2014527419 A | 10/2014 |
| JP | 2015016379 A | 1/2015 |
| WO | 9723172 A2 | 7/1997 |
| WO | 2005006993 A2 | 1/2005 |
| WO | 2010151564 A1 | 12/2010 |
| WO | 2011075697 A2 | 6/2011 |
| WO | 2013003433 A1 | 1/2013 |
| WO | 2014143538 A1 | 9/2014 |
| WO | 2017155995 A1 | 9/2017 |
| WO | 2017160889 A1 | 9/2017 |
| WO | 2017204832 A1 | 11/2017 |

OTHER PUBLICATIONS

Notice of Reasons for Refusal, JP Application No. 2021-554720, Dec. 5, 2023 (7 pages).
First Office Action CN Application No. 202080020406.X, Jan. 30, 2024 (9 pages).
Examination Report EP Application No. 20718018.3, Jan. 10, 2024 (6 pages).
Hossain, Fahad et al: "Knee Arthroplasty With a Medially Conforming Ball-and-Sock Tibiofemoral Articulation Provides Better Function", Annual Meeting of the Knee Society, vol. 469, No. 1, Jan. 1, 2011 (Jan. 1, 2011), pp. 55-63, XP055947606.
Shimmin Andrew et al.: "Fluoroscopic Motion Study Confirming the Stability of a Medial Pivot Design Total Knee Arthroplasty", The Knee, Elsevier, Amsterdam, NL, vol. 22, No. 6, Dec. 7, 2014 (Dec. 7, 2014), pp. 522-526, XP029361524, ISSN: 0968-0160, DOI: 10.1016/J.KNEE.2014.11.011.
Morra, A., et al: "Virtual Geometric Constraint of Total Knee Arthroplasty Designs: Addressing Patient Needs", Orthopaedic Research Laboratories, Mar. 1, 2016 (Mar. 1, 2016), XP055947619.
Anonymous: "GMK Sphere Medially Stabillized Knee", Sep. 1, 2019 (Sep. 1, 2019), pp. 1-24, XP093115521.
Anonymous: "MedActa Announces 100,000 GMK Sphere Implanted Worldwide", Jun. 24, 2021 (Jun. 24, 2021), XP093115522, Retrieved From the Internet: URL:https://www.medacta.com/gr/news-detaipid-15123#atext=gmk%20sphere%2c.
Third Party Observation, European Patent Appln. No. 20718018.3, Jul. 8, 2022, 7 Pages.
Advance, Medial-Pivot and Stemmed Medial-Pivot Knee Systems, Wright Medical Technology, Inc., 2010, 12 pages.
Persona, The Personalized Knee, Surgical Technique, Zimmer Biomet, 2018, 76 pages.
Persona, The Personalized Knee, Medial Congruent Bearing Design Rationale, Zimmer Biomet, 2017, 20 pages.
EMP, Evolution, Medial-Pivot Knee System, The ACL-PCL Substituting Knee, Key Aspects, MicroPort Orthopaedics, 2015, 6 pages.
Evolution, Medial-Pivot Knee System, Surgical Technique, Distal Cut First, MicroPort Orthopaedics, 2014, 52 pages.
PCT Search Report & Written Opinion prepared for PCT/EP2021/069244, mailed Nov. 1, 2022, 24 pages.
Smith & Nephew, Journey II TKA Total Knee System—Combined Technique for Journey II BCS and Journey II CR, 68 pages.
International SR and Written Opinion for International App. No. PCT/US2020/022123, Completed May 8, 2020, 13 Pages.
International SR for International App. No. PCT/IB20/54105, Aug. 31, 2020, 3 Pages.
PCT International SR for International App. No. PCT/IB20/54110, Aug. 12, 2020, 3 Pages.
PCT International SR and Written Opinion for International App. No. PCT/EP2020/075246, Mar. 15, 2022, 11 Pages.
International Search Report and Written Opinion for International Application No. PCT/US2020/022119, completed May 27, 2020, 11 pages.

* cited by examiner

ORTHOPAEDIC SYSTEM WITH MEDIAL PIVOTING FEMORAL COMPONENT AND INSERT

CROSS-REFERENCE TO RELATED APPLICATIONS

This patent application is the U.S. national phase application of PCT/US2020/022119, which was filed on Mar. 11, 2020, and which claims priority to and the benefit of U.S. Provisional Patent Application Ser. No. 62/817,173 entitled "ORTHOPAEDIC SYSTEM WITH MEDIAL PIVOTING FEMORAL COMPONENT AND INSERT," which was filed on Mar. 12, 2019, the disclosures of both of which are hereby expressly incorporated by reference into this application.

TECHNICAL FIELD

The present invention relates to orthopaedic systems, and, more particularly, to orthopaedic systems for performing knee replacement surgery.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. Depending on the severity of the damage to the patient's joint, orthopaedic prostheses of varying mobility may be used. For example, the knee prosthesis may include a "fixed" tibial insert in cases wherein it is desirable to limit the movement of the knee prosthesis, such as when significant soft tissue damage or loss is present. Alternatively, the knee prosthesis may include a "mobile" tibial insert in cases wherein a greater degree of freedom of movement is desired. Additionally, the knee prosthesis may be a total knee prosthesis designed to replace the femoral-tibial interface of both condyles of the patient's femur or a uni-compartmental (or uni-condylar) knee prosthesis designed to replace the femoral-tibial interface of a single condyle of the patient's femur.

The type of orthopedic knee prosthesis used to replace a patient's natural knee may also depend on whether the patient's posterior cruciate ligament is retained or sacrificed (i.e., removed) during surgery. For example, if the patient's posterior cruciate ligament is damaged, diseased, and/or otherwise removed during surgery, a posterior-stabilized knee prosthesis may be used to provide additional support and/or control at later degrees of flexion. Alternatively, if the posterior cruciate ligament is intact, a cruciate-retaining knee prosthesis may be used.

Typical orthopaedic knee prostheses are generally designed to duplicate the natural movement of the patient's joint. As the knee is flexed and extended, the femoral and tibial components articulate and undergo combinations of relative anterior-posterior motion and relative internal-external rotation. However, the patient's surrounding soft tissue also impacts the kinematics and stability of the orthopaedic knee prosthesis throughout the joint's range of motion. That is, forces exerted on the orthopaedic components by the patient's soft tissue may cause unwanted or undesirable motion of the orthopaedic knee prosthesis. For example, the orthopaedic knee prosthesis may exhibit an amount of unnatural (paradoxical) anterior translation as the femoral component is moved through the range of flexion.

SUMMARY

The present disclosure provides an orthopaedic system with tibial insert that is configured to allow asymmetric pivoting of a femoral component bearing on the tibial insert, a raised anterior medial surface that is conforming to the femoral component, and geometry to provide stability.

According to an aspect of the disclosure, an orthopaedic system may include a tibial insert and a femoral component. The tibial insert may include a medial articular surface and a lateral articular surface. The medial and lateral articular surfaces may be asymmetrically shaped relative to each other. The femoral component may include a medial condyle configured to articulate on the medial articular surface of the tibial insert and a lateral condyle configured to articulate on the lateral articular surface of the tibial insert. The medial condyle of the femoral component includes a femoral articular surface having a first radius of curvature that extends posteriorly to a first degree of flexion of 70 degrees or less and a plurality of decreasing radii of curvature that extend posteriorly from the first degree of flexion to a second degree of flexion greater than the first degree of flexion.

In some embodiments, the femoral articular surface of the femoral component has a second radius of curvature at the second degree of flexion. In such embodiments, the second radius of curvature may be greater than the posterior-most radius of the plurality of decreasing radii of curvature. Additionally or alternatively, the femoral articular surface of the femoral component may have a second radius of curvature, posterior of the decreasing radii of curvature, that is greater than the posterior-most radius of the plurality of decreasing radii of curvature.

Additionally, in some embodiments, the medial articular surface of the tibial insert and the femoral articular surface of the medial condyle of the femoral component are more conforming than the lateral articular surface of the tibial insert and femoral articular surface of the lateral condyle of the femoral component. For example, the medial articular surface and the femoral articular surface of the medial condyle may have an anterior-posterior conformity of at least 96% at zero degrees of flexion. Additionally or alternatively, the medial articular surface of the tibial insert and the femoral articular surface of the medial condyle may have a medial-lateral conformity of at least 93%. Additionally or alternatively, the lateral articular surface of the tibial insert and the femoral articular surface of the lateral condyle may have a medial-lateral conformity of at least 93%.

In some embodiments, the tibial insert includes an anterior medial lip having a first height and an anterior lateral lip having a second height. In such embodiments, the first height of the anterior medial lip is greater than the second height of the anterior lateral lip. Additionally, the medial articular surface of the tibial insert may include a dwell point, and the first height of the anterior medial lip, relative to the dwell point, may be at least 9 millimeters. Additionally or alternatively, the medial articular surface of the tibial insert may include a dwell point having an arcuate or oblong shape when viewed in a transverse plane.

In some embodiments, the medial articular surface of the tibial insert includes a dwell point and an anterior medial lip. In such embodiments, the anterior medial lip has a height, relative to the dwell point, of at least 9 millimeters. Additionally, in some embodiments, the medial articular surface of the tibial insert may include a dwell point having an arcuate or oblong shape when viewed in a transverse plane. Further, in some embodiments, the first radius of curvature has a length that is between 41% to 47% of an anterior-posterior length of the tibial insert. In some embodiments, the medial articular surface of the tibial insert includes a dwell point, and the lateral articular surface provides an arcuate path for pivoting of the femoral component about the dwell point. Additionally, in some embodiments, the first radius of curvature may extend anteriorly to a hyper-extension degree of flexion of 30 degrees or less.

According to another aspect, a tibial insert of a knee replacement system includes a lateral articular surface and a medial articular surface. The lateral articular surface may be configured to articulate with a lateral condyle of a femoral component. Similarly, the medial articular surface may be configured to articulate with a medial condyle of the femoral component. Additionally, the medial articular surface is asymmetrically shaped relative to the lateral articular surface and includes a dwell point and an anterior medial lip having a height, relative to the dwell point, of at least nine millimeters.

In some embodiments, the medial articular surface and the medial condyle of the femoral component are more conforming than the lateral articular surface and the lateral condyle of the femoral component. Additionally, in some embodiments, the dwell point has an arcuate or oblong shape when viewed in a transverse plane. Furthermore, in some embodiments, the lateral articular surface may include an anterior lateral lip having a height less than the height of the anterior medial lip.

According to yet another aspect, an orthopaedic system may include a tibial insert and a femoral component. The tibial insert may include a lateral articular surface and a medial articular surface. The femoral component may include a medial condyle configured to articulate on the medial articular surface of the tibial insert and a lateral condyle configured to articulate on the lateral articular surface of the tibial insert. The medial condyle of the femoral component may include a femoral articular surface having a first radius of curvature that extends posteriorly to a first degree of flexion of 70 degrees or less and a plurality of decreasing radii of curvature that extend posteriorly from the first degree of flexion to a second degree of flexion greater than the first degree of flexion. Additionally, the medial articular surface of the tibial insert is asymmetrically-shaped relative to the lateral articular surface and includes a dwell point having an arcuate or oblong shape and an anterior medial lip having a height, relative to the dwell point, of at least nine millimeters.

In some embodiments, the tibial insert may include an anterior lateral lip and, in such embodiments, the height of the anterior medial lip is greater than a height of the anterior lateral lip. Additionally, in some embodiments, the femoral articular surface of the femoral component has a second radius of curvature at the second degree of flexion. the second radius of curvature may be greater than the posterior-most radius of the plurality of decreasing radii of curvature. In some embodiments, the second radius of curvature may be posterior of the decreasing radii of curvature.

Additionally, in some embodiments, the medial articular surface of the tibial insert and the femoral articular surface of the medial condyle of the femoral component may be more conforming than the lateral articular surface of the tibial insert and femoral articular surface of the lateral condyle of the femoral component. For example, the medial articular surface of the tibial insert and the femoral articular surface of the medial condyle may have a medial-lateral conformity of at least 93%. In some embodiments, the lateral articular surface may provide an arcuate path for pivoting of the femoral component about the dwell point. Additionally, in some embodiments, the first radius of curvature may extend anteriorly to a hyper-extension degree of flexion of 30 degrees or less.

According to yet another aspect, an orthopaedic system includes a tibial insert and a femoral component. The tibial insert may have an articular surface, and the femoral component may have a condyle configured to articulate on the articular surface of the tibial insert. The condyle of the femoral component may include a femoral articular surface having a first radius of curvature that extends posteriorly to a first degree of flexion of 70 degrees or less and a plurality of decreasing radii of curvature that extend posteriorly from the first degree of flexion to a second degree of flexion greater than the first degree of flexion. The articular surface of the tibial insert may include a dwell point having an arcuate or oblong shape when viewed in a transverse plane and an anterior lip having a height, relative to the dwell point, of at least nine millimeters.

In some embodiments, the femoral articular surface of the femoral component has a second radius of curvature at the second degree of flexion. In such embodiments, the second radius of curvature may be greater than the posterior-most radius of the plurality of decreasing radii of curvature. Additionally, in some embodiments, the second radius of curvature is posterior of the decreasing radii of curvature. Furthermore, in some embodiments, the articular surface of the tibial insert and the femoral articular surface of the condyle may have a medial-lateral conformity of at least 93%.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and orthopaedic surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise.

Figure 1:
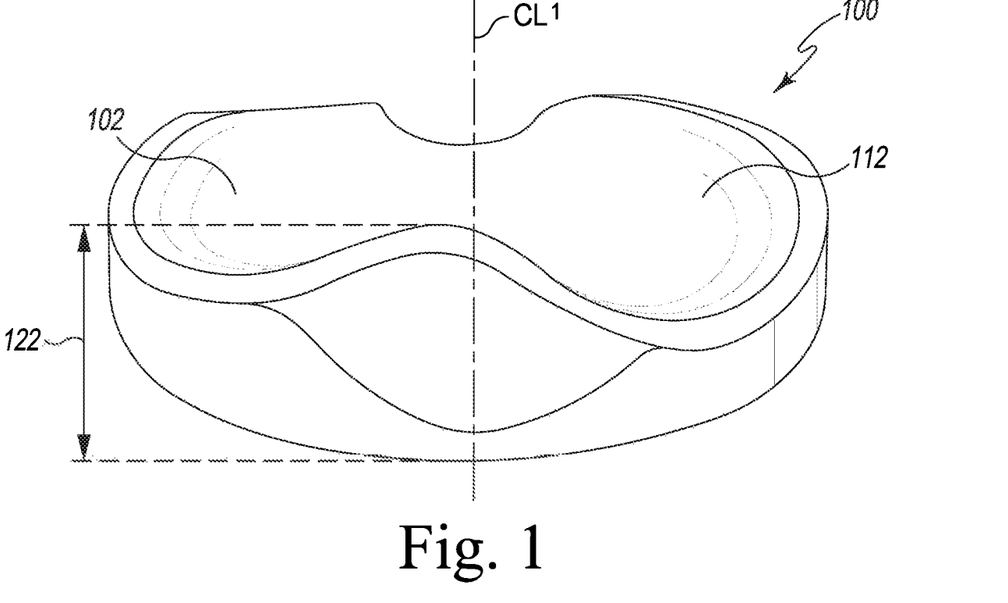
FIG. 1 is a front perspective view of tibial insert having asymmetric articular surfaces.
Figure 2:
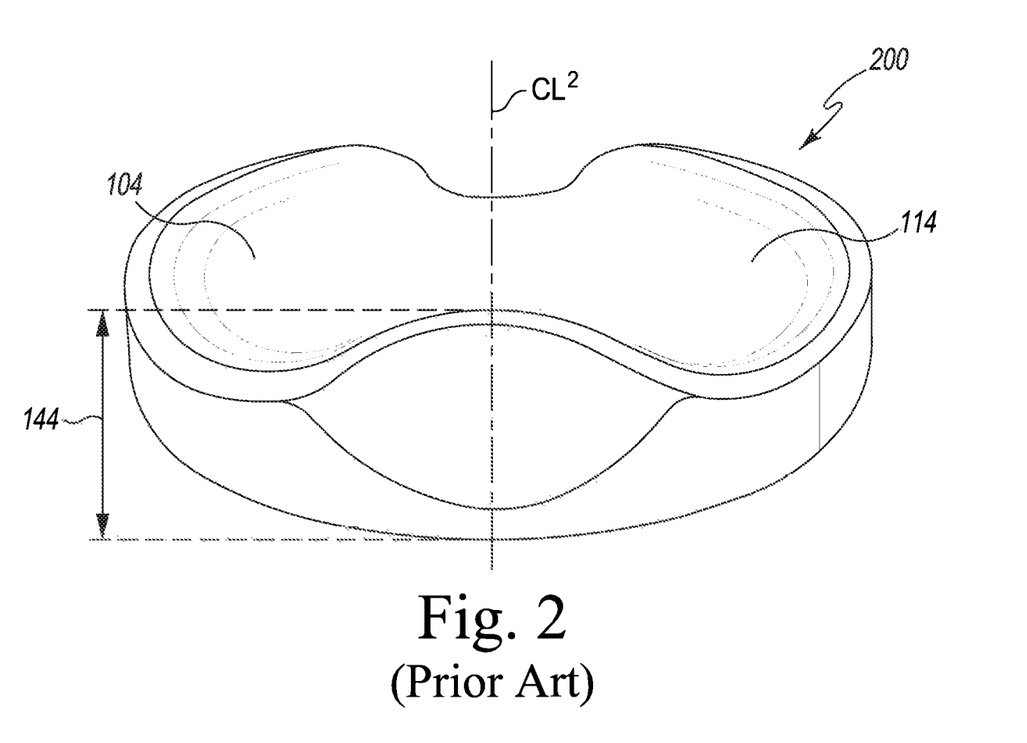
FIG. 2 is a front perspective view of a known tibial insert having symmetric articular surfaces.

Referring now to the drawings, and more particularly to FIG. 1, an illustrative embodiment of a tibial insert 100 provided in accordance with the present disclosure is illustrated. For comparison, a known tibial insert 200 is illustrated in FIG. 2. Each tibial insert 100, 200 defines a respective anterior-posterior centerline CL1, CL2 and a medial articular surface 102, 104 on one half of the centerline CL1, CL2, respectively, and a lateral articular surface 104, 114 on the other half of the centerline CL1, CL2, respectively. Unlike the known tibial insert 200, the articular surfaces 102, 112 of the tibial insert 100 are asymmetrically-shaped to provide asymmetric pivoting of a femoral component bearing on the tibial insert 100. The medial articular surface 102 of the tibial insert 100 is more conforming to, for example, a condylar portion of a femoral component than the medial articular surface 104 of the tibial insert 200, as will be described further herein. The tibial insert 100 also has a relatively raised anterior surface (anterior medial lip height 122) on a medial side of the tibial insert 100, compared to the tibial insert 200 (anterior medial lip height 144).

Figure 3A:
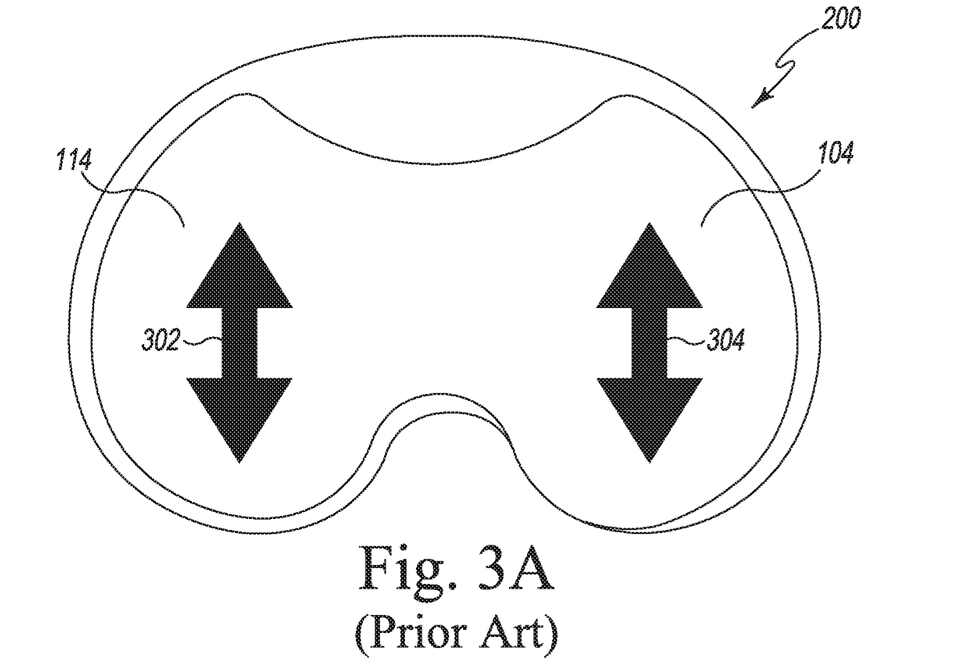
FIG. 3A is a superior view of the known tibial insert of FIG. 2.
Figure 3B:
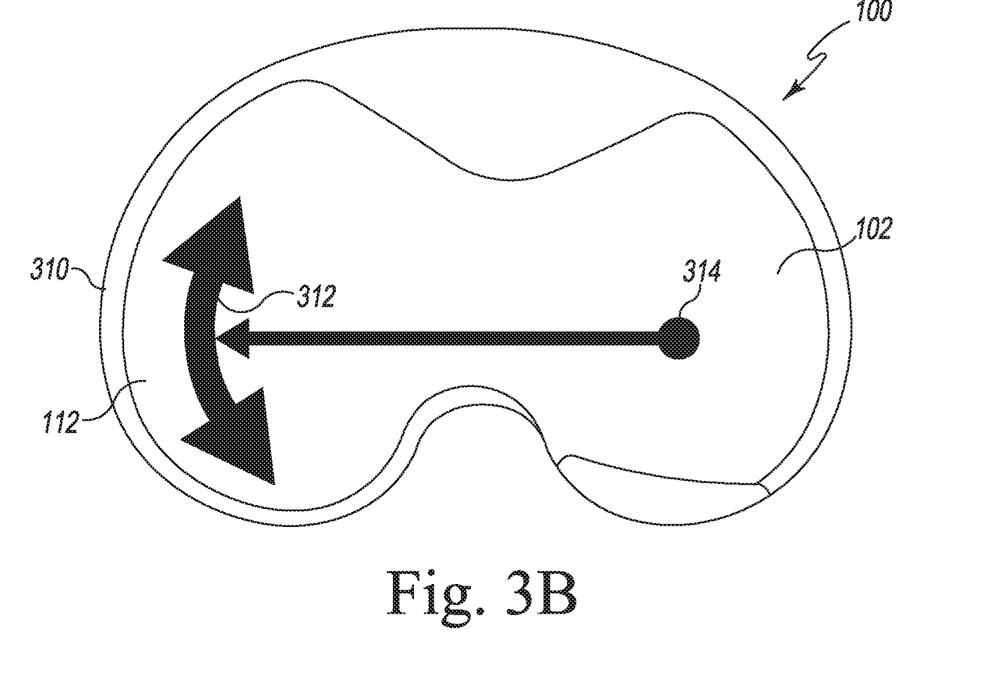
FIG. 3B is a superior view of the orthopaedic insert of FIG. 1.

With continued reference to FIG. 1, and referring now to FIG. 3B as well, a lateral side 310 of the tibial insert 100 provides an arcuate path 312, denoted by a curved arrow, for pivoting of the femoral component about a medial pivot point 314 extending through the medial articular surface 102. The arcuate path 312 may be laterally centered on the medial pivot point 314. This pivoting motion differs from the motion path 302, 304 of a femoral component bearing on the tibial insert 200, which is symmetric as shown in FIG. 3A. Thus, the tibial insert 100, unlike the tibial insert 200, provides a medial pivot point for a femoral component bearing on the tibial insert 100.

Figure 4:
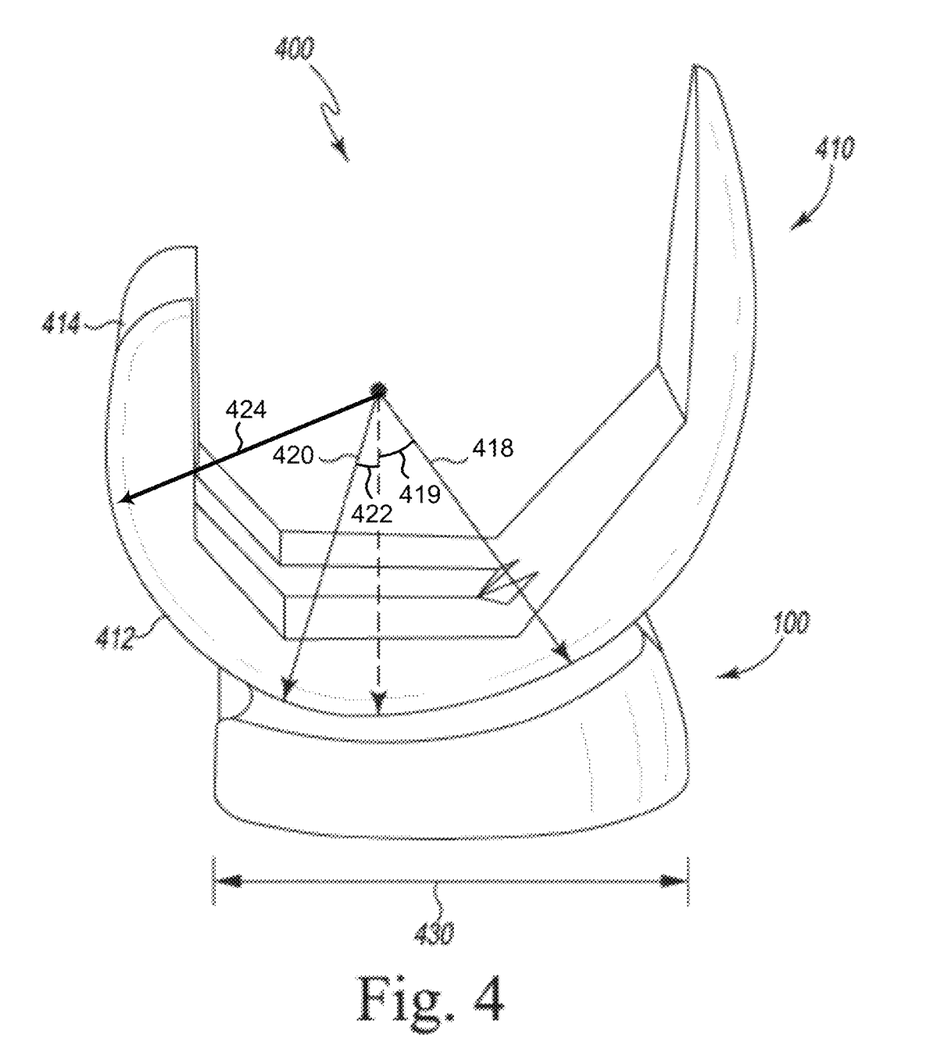
FIG. 4 is a side perspective view of an orthopaedic system including a femoral component and the tibial insert of FIGS. 1 and 3B.

Referring now to FIG. 4, an orthopaedic system 400 including a femoral component 410 bearing on the tibial insert 100 illustrated in FIGS. 1 and 3B is illustrated. The femoral component 410 includes a medial femoral condyle 412 configured to articulate on the medial articular surface 102 of the tibial insert 100 and a lateral femoral condyle 414 configured to articulate on the lateral articular surface 112. One or both of the femoral condyles 412, 414 may define a radius of curvature that extends anteriorly between 10 and 30 degrees. One or both of the femoral condyles 412, 414 may define a radius of curvature 418 that extends anteriorly a degree of hyper-extension 419 of 30 degrees or less. Additionally, as shown in FIG. 4, the femoral component 410 may define a constant radius of curvature 420 that extends posteriorly to a degree of flexion 422 between 30 and 70 degrees before starting to gradually decrease in radii of curvature that define a remainder of a sagittal shape of the femoral component 410 subsequent to the degree of flexion 422. The femoral component 410 may define a constant radius of curvature that may extend posteriorly to a degree of flexion 422 of 70 degrees or less before starting to gradually decrease in radii of curvature that define a remainder of a sagittal shape of the femoral component. The femoral component 410 may include a second radius of curvature 424 at a degree of flexion posterior to the decreasing radii of curvature. The second radius of curvature 424 may be greater than each of the decreasing radii of curvature. For example, the second radius of curvature 424 may be greater than the posterior-most radius of the decreasing radii of curvature.

For a medial conforming design with a series of radii of curvatures, the choice of conformity is important in defining the ability to resist paradoxical translation. Some embodiments of the femoral component 410 may have the constant radius of curvature 420 extend to a degree of flexion of 30 degrees or less and have subsequently reducing radii of curvature for a range of degrees of flexion thereafter. Some embodiments may have a radius of curvature 420 that can extend to a degree of flexion of 70 degrees or less and then include a few radii of curvature of much smaller size to define the posterior condyle sagittal shape in deep flexion. For a natural medial pivoting motion, some embodiments may have a range of higher conformity on the medial side for stability, plus a series of smaller radii of curvature to restore normal gait in deeper flexion angles. The articular surface of the lateral femoral condyle 414 is generally less conforming sagittally than the articular surface of the medial femoral condyle 412. The lateral tibial surface has an arcuate shape that is generally centered around the lowest position or dwell point/region of the medial conforming surface. In that way, the dwell point acts as the medial pivot point for the femoral component bearing on the tibial insert 100.

The relationship of the anterior-posterior (AP) length 430 of the tibial insert 100 to the size of the radius of curvature 418 of the femoral component 410 is important. If the radius of curvature of 418 and/or radius of curvature 420 is too large (depending on the particular degree of flexion), a booking or hinge effect can occur in mid flexion. If the radius of curvature 420 is too small, the series of radii of curvature may need to increase at some point to obtain the needed anterior-posterior dimension of the implant. In some embodiments, the radius of curvature 420 may be between 41% and 47% of the anterior-posterior length of the tibial insert 100. A ratio of coronal curvature to sagittal curvature for the radius of curvature defining that section of the femoral component 410 may be between, for example, 41% to 100%.

Referring now to FIGS. 5A-5E, the geometry of the tibial insert 100 is illustrated. As previously described, the medial articular surface 102 of the tibial insert 100 conforms to the femoral component 410. An anterior-posterior surface conformity of the medial articular surface 102 may be at least 96% of the radius of curvature 420 the femoral component 410 (e.g., at zero degrees of flexion). For example, the anterior-posterior conformity between the medial articular surface 102 and the corresponding femoral articular surface of the femoral component 410 may be 96% or greater (e.g., at zero degrees of flexion). The medial-lateral conformity of the medial and lateral articular surfaces 102, 112 may be at least 93% of a medial-lateral condylar radius of curvature of the femoral component 410. For example, the medial-lateral conformity between the medial and lateral articular surfaces 102, 112 and the corresponding femoral articular surfaces of the femoral component 410 may be 93% or greater.

For optimal medial stability, it is necessary to extend the extension radius forward by 20-30 degrees. Although a natural knee does not hyperextend to these degrees, the matching conformity on the tibial surface creates a taller medial anterior surface than in most designs. A minimal height of an anterior medial lip 502 (see FIG. 5E) may have a height 504 of at least 9 mm higher than the lowest dwell point 506 (See FIG. 5A) on the medial articular surface 102. This taller surface increases the overall conformity of the medial articular surface 102 and can reduce the likelihood of dislocation if the height of the surface is 9 mm or greater than the lowest articular surface region or dwell point 506. The medial dwell point 506 may be a curved dwell with the shape of an arc or may be oblong with a flat surface of no more than 1 mm between two curved surfaces.

Figure 5A:
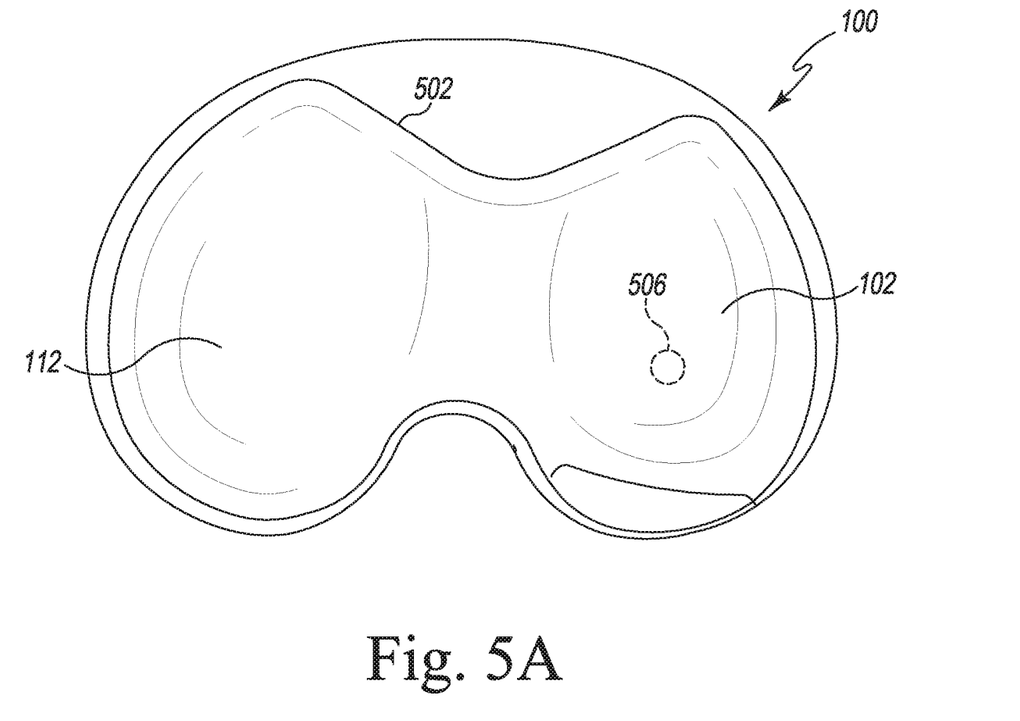
FIG. 5A is a superior view of the tibial insert of FIGS. 1 and 3B.
Figure 5B:
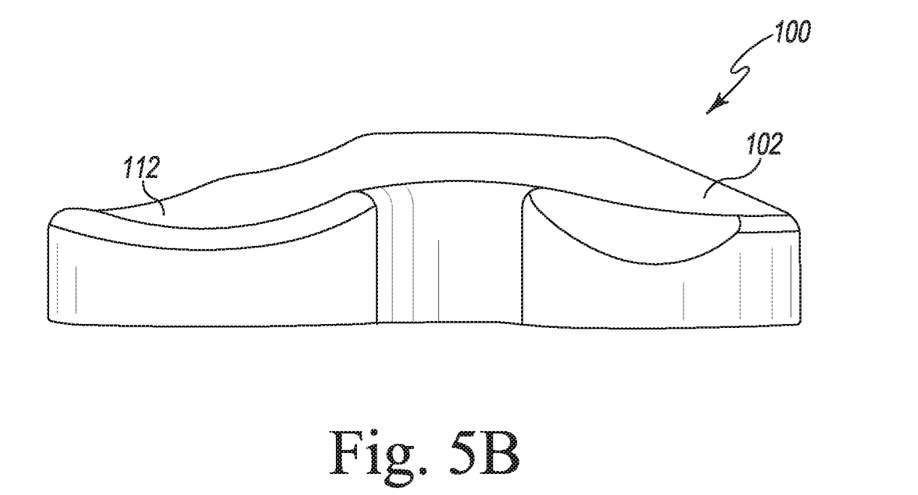
FIG. 5B is a rear elevation view of the tibial insert of FIGS. 1 and 3B.
Figure 5C:
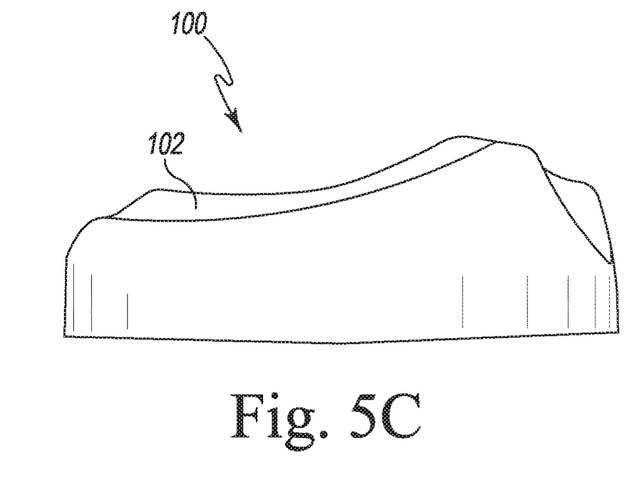
FIG. 5C is a medial side view of the tibial insert of FIGS. 1 and 3B.
Figure 5D:
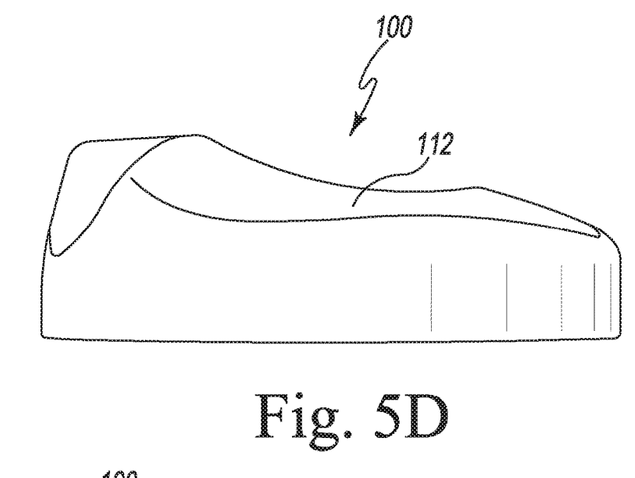
FIG. 5D is a lateral side of the orthopaedic insert of FIGS. 1 and 3B.
Figure 5E:
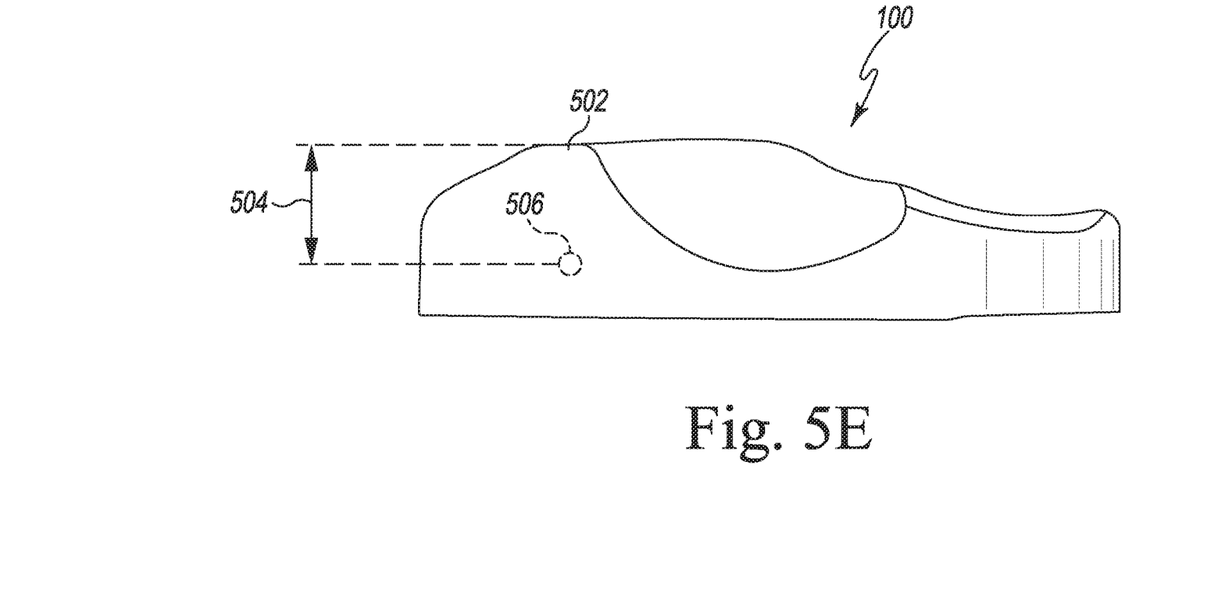
FIG. 5E is a front elevation view of the tibial insert of FIGS. 1 and 3B.

Another feature of the tibial insert 100 is the location of the dwell point 506 on the medial articular surface 102. If the medial dwell point 506 is too far forward, the artificial knee may not be able to achieve deeper flexion angles without removing the posterior conformity on the tibial surface. If the dwell point 506 on the medial articular surface 102 is too far posterior, the anterior surface of the medial articular surface 102 will have difficulty in obtaining necessary extension of the artificial knee and excessive posterior loading through the tibia may induce some loosening of the tibial insert 100 from the cement. Dwell positions on both the medial and lateral articular surfaces 102, 112 can be in line with respective condylar portions of the femoral component 410.

Regarding the ratio of conformity of the medial and lateral condylar surfaces of the femoral component 410, the ratio is important in defining a pivoting motion. If the coronal radius is too flat, the ability of the implant or orthopaedic system to rotate and maintain anterior stability is compromised.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. An orthopaedic system comprising:
    a tibial insert having a medial articular surface and a lateral articular surface, wherein the medial and lateral articular surfaces are asymmetrically shaped relative to each other; and
    a femoral component having a medial condyle configured to articulate on the medial articular surface of the tibial insert and a lateral condyle configured to articulate on the lateral articular surface of the tibial insert, wherein the medial condyle of the femoral component includes a femoral articular surface having a first radius of curvature that extends posteriorly to a first degree of flexion of 70 degrees or less and a plurality of decreasing radii of curvature that extend posteriorly from the first degree of flexion to a second degree of flexion greater than the first degree of flexion,
    wherein the medial articular surface of the tibial insert and the femoral articular surface of the medial condyle have a medial-lateral conformity of at least 93%, and
    wherein the lateral articular surface of the tibial insert and the femoral articular surface of the lateral condyle have a medial-lateral conformity of at least 93%.

2. The orthopaedic system of claim 1, wherein the femoral articular surface of the femoral component has a second radius of curvature at the second degree of flexion, the second radius of curvature being greater than each of the decreasing radii of curvature.

3. The orthopaedic system of claim 1, wherein the femoral articular surface of the femoral component has a second radius of curvature, posterior of the decreasing radii of curvature, that is greater than the posterior-most radius of the plurality of decreasing radii of curvature.

4. The orthopaedic system of claim 1, wherein the medial articular surface of the tibial insert and the femoral articular surface of the medial condyle of the femoral component are more conforming than the lateral articular surface of the tibial insert and femoral articular surface of the lateral condyle of the femoral component.

5. The orthopaedic system of claim 1, wherein the medial articular surface of the tibial insert includes a dwell point and an anterior medial lip, wherein the anterior medial lip has a height, relative to the dwell point, of at least 9 millimeters.

6. The orthopaedic system of claim 1, wherein the medial articular surface of the tibial insert includes a dwell point having an arcuate or oblong shape when viewed in a transverse plane.

7. The orthopaedic system of claim 1, wherein the first radius of curvature has a length that is between 41% to 47% of an anterior-posterior length of the tibial insert.

8. The orthopaedic system of claim 1, wherein the medial articular surface of the tibial insert includes a dwell point and the lateral articular surface provides an arcuate path for pivoting of the femoral component about the dwell point.

9. The orthopaedic system of claim 1, wherein the first radius of curvature extends anteriorly to a hyper-extension degree of flexion of 30 degrees or less.

10. An orthopaedic system comprising:
    a tibial insert comprising a lateral articular surface and a medial articular surface, and
    a femoral component comprising a medial condyle configured to articulate on the medial articular surface of the tibial insert, and a lateral condyle configured to articulate on the lateral articular surface of the tibial insert, the medial condyle of the femoral component including a femoral articular surface having a first radius of curvature that extends posteriorly to a first degree of flexion of 70 degrees or less and a plurality of decreasing radii of curvature that extend posteriorly from the first degree of flexion to a second degree of flexion greater than the first degree of flexion,
    wherein the medial articular surface of the tibial insert is asymmetrically-shaped relative to the lateral articular surface and includes a dwell point having an arcuate or oblong shape when viewed in a transverse plane and an anterior medial lip having a height, relative to the dwell point, of at least nine millimeters, and
    wherein the medial articular surface of the tibial insert and the femoral articular surface of the medial condyle have a medial-lateral conformity of at least 93%.

11. The orthopaedic system of claim 10, wherein the tibial insert includes an anterior lateral lip, and wherein the height of the anterior medial lip is greater than a height of the anterior lateral lip.

12. The orthopaedic system of claim 10, wherein the femoral articular surface of the femoral component has a second radius of curvature at the second degree of flexion, wherein the second radius of curvature is greater than the posterior-most radius of the plurality of decreasing radii of curvature.

13. The orthopaedic system of claim 10, wherein the medial articular surface of the tibial insert and the femoral articular surface of the medial condyle of the femoral component are more conforming than the lateral articular surface of the tibial insert and femoral articular surface of the lateral condyle of the femoral component.

14. The orthopaedic system of claim 10, wherein the first radius of curvature extends anteriorly to a hyper-extension degree of flexion of 30 degrees or less.

\* \* \* \* \*